(12) United States Patent
Baumgartl et al.

(10) Patent No.: US 10,386,431 B2
(45) Date of Patent: Aug. 20, 2019

(54) MAGNETIC RESONANCE TOMOGRAPHY WITH SLOW TEMPERATURE VARIATION COMPENSATION

(71) Applicants: Rudi Baumgartl, Erlangen (DE); Andrew Dewdney, Neunkirchen am Brand (DE)

(72) Inventors: Rudi Baumgartl, Erlangen (DE); Andrew Dewdney, Neunkirchen am Brand (DE)

(73) Assignee: Siemens Healthcare GmbH, Erlangen (DE)

( * ) Notice: Subject to any disclaimer, the term of this patent is extended or adjusted under 35 U.S.C. 154(b) by 65 days.

(21) Appl. No.: 15/698,146

(22) Filed: Sep. 7, 2017

(65) Prior Publication Data

US 2018/0074141 A1 Mar. 15, 2018

(30) Foreign Application Priority Data

Sep. 13, 2016 (DE) .................. 10 2016 217 420

(51) Int. Cl.
*G01R 33/58* (2006.01)
*G01R 33/48* (2006.01)
(Continued)

(52) U.S. Cl.
CPC .......... *G01R 33/389* (2013.01); *G01R 33/31* (2013.01); *G01R 33/4804* (2013.01);
(Continued)

(58) Field of Classification Search
CPC .. G01R 33/389; G01R 33/31; G01R 33/4804; G01R 33/583; G16H 40/40; G01K 13/00
See application file for complete search history.

(56) References Cited

U.S. PATENT DOCUMENTS

| 8,797,032 B2 * | 8/2014 | Ookawa | A61B 5/055 324/314 |
| 2014/0084917 A1 | 3/2014 | Dewdney | |
| 2014/0239950 A1 | 8/2014 | Ookawa | |

FOREIGN PATENT DOCUMENTS

DE 102012217594 B4 11/2015

OTHER PUBLICATIONS

German Office Action for German Application No. 102016217420.7, dated May 22, 2017.

* cited by examiner

*Primary Examiner* — Rodney A Bonnette
(74) *Attorney, Agent, or Firm* — Lempia Summerfield Katz LLC

(57) ABSTRACT

A magnetic resonance tomography system has a frequency control device for temperature compensation, a temperature sensor, and a high frequency generator. An output frequency of an output signal from the high frequency generator is dependent on a value of a digital frequency variable, and a synthesis signal with the system frequency is generated dependent on the output signal. A temperature change is detected using the temperature sensor, a temperature-time function of the temperature is determined using the temperature change that has been detected, a time is determined at which a change in the digital frequency variables in the least significant bit brings about a change in the frequency of the synthesis signal that corresponds with a change in the system frequency due to a temperature, according to the interpolated temperature-time function, and the digital frequency variable in the least significant bit is changed at the specified time.

20 Claims, 2 Drawing Sheets

(51) Int. Cl.
  *G01R 33/31* (2006.01)
  *G16H 40/40* (2018.01)
  *G01R 33/389* (2006.01)
  *G01K 13/00* (2006.01)
(52) U.S. Cl.
  CPC ........... *G01R 33/583* (2013.01); *G16H 40/40* (2018.01); *G01K 13/00* (2013.01)

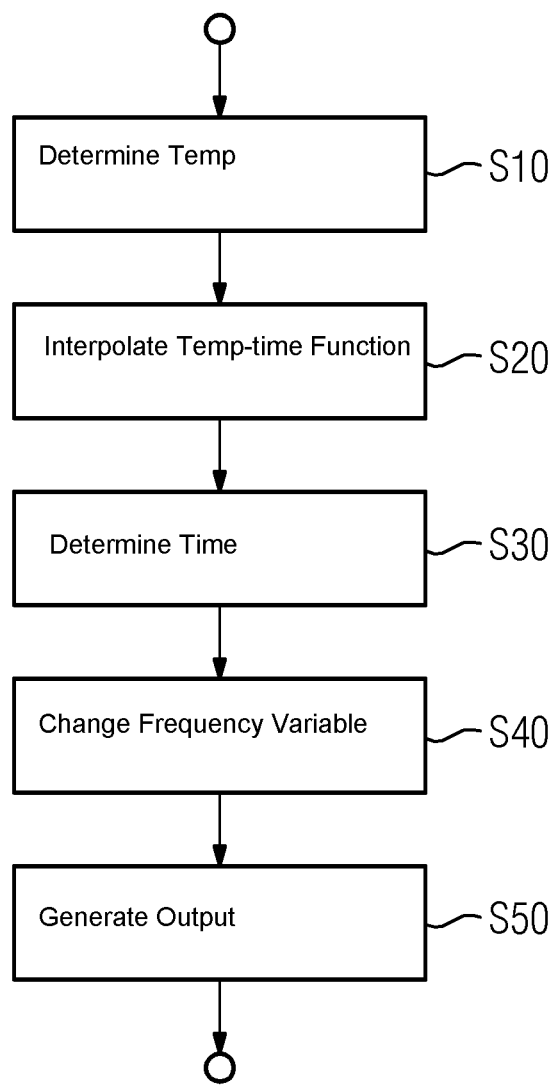

MAGNETIC RESONANCE TOMOGRAPHY WITH SLOW TEMPERATURE VARIATION COMPENSATION

RELATED CASE

This application claims the benefit of DE 102016217420.7, filed on Sep. 13, 2016, which is hereby incorporated by reference in its entirety.

FIELD

The present embodiments relate to a magnetic resonance tomography system with a device to compensate for slow temperature variations and a method for operating the magnetic resonance tomography system. The magnetic resonance tomography system includes a temperature sensor and a high frequency generator. A system frequency of the magnetic resonance tomography system has a temperature dependence on a temperature and the temperature sensor is designed to detect this temperature.

BACKGROUND

Magnetic resonance tomography systems are imaging devices that align nuclear spins of the examination subject with a strong external magnetic field in order to create an image of an examination subject and excite the spins into precession around this alignment using an alternating magnetic field. The precession or return of the spins from this excited state to a state with less energy in turn generates a responsive alternating magnetic field, also known as a magnetic resonance signal, which is received using antennas.

With the aid of magnetic gradient fields, a spatial encoding is imprinted on the signals that subsequently allows the received signal to be assigned to a volume element. The received signal is then evaluated and a three-dimensional image of the examination subject is provided. The image generated indicates a spatial density distribution of the spins.

In a constant, homogeneous magnetic field $B_0$, the resonance frequency of the nuclear spins falls within a very narrow band (a few hertz to kilohertz) around what is known as the Larmor frequency. A non-homogeneous $B_0$ field leads to a spatial variation in the resonance frequency, and a global change in the strength of the magnetic field leads to the center being moved. If the $B_0$ field changes without the frequency and spectral distribution of the excitation pulses being adjusted, then the excitation of the nuclear spins via the excitation pulse by the $B_1$ field is not sufficient and leads to a weak signal or has spatial gaps. Unwanted changes in the time-dependent magnetic field components, due for example to eddy currents generated by the gradient coils for spatial encoding likewise lead to such effects. In order to overcome this problem, it is possible, for example, to broaden the bandwidth of the excitation pulses, leading, however, to greater radiation exposure of the patient through absorbed radio waves and restricting the maximum output due to limiting values.

Variations in the magnetic field occur among other things as a result of temperature changes in components that have temperature-dependent magnetic properties, such as, for example, the outer shell of the cryostat or of the gradient coils themselves.

Document DE 10 2012 2017 594 B4 discloses a magnetic resonance tomography system including a frequency control device and a temperature sensor that controls a frequency of the excitation pulse as a function of the temperature signal.

The narrow bandwidth and the temperature dependency lead, however, to temperature changes in the milli-Kelvin range becoming relevant. In order to avoid additional noise components through compensating for this, an averaging of the temperature measurement ensues over fairly long periods, subsequently leading to greater frequency shifts when the measured temperature change is converted after an averaging period and thus to artifacts in the imaging.

SUMMARY AND DETAILED DESCRIPTION

It is therefore an object of the present embodiments to provide a magnetic resonance tomography system with improved imaging.

The object is achieved by a magnetic resonance tomography system as provided in any of the embodiments herein. The scope of the present invention is defined solely by the appended claims and is not affected to any degree by the statements within this summary.

The magnetic resonance tomography system includes a frequency control device for temperature compensation, a temperature sensor, and a high frequency generator. A system frequency has a temperature dependence on a temperature, and the temperature sensor is designed to measure this temperature.

Here the system frequency can be defined, for example, as any frequency of the magnetic resonance tomography system that contributes to the generation of the excitation pulse, such that in the event of a change in the system frequency, the frequency of the excitation pulse would likewise change. There can be a mixed frequency or a signal that is multiplied to generate the excitation signal in the frequency. However, the system frequency may be a signal required for receiving nuclear spin resonance signals from the examination subject, for example, a mixed frequency for a receiver. Here the system frequency can also be the frequency of a digital signal in a digital signal generation system or a digital receiver.

Here, temperature dependence on a temperature is defined not only as a direct temperature dependence where the temperature change directly changes the frequency by, for example, a resonance element in an oscillator changing its electrical value through the temperature. Temperature dependence is also, however, to be defined, for example, more in the sense of temperature-dependent changes in a magnetic field that change the Larmor frequency and thus also require a change in the signals and system frequencies generated in the magnetic resonance tomography system, in order to continue to receive a resonance signal from the nuclear spins.

The temperature sensor is designed to determine a temperature change in this temperature, leading either indirectly, through a change in the $B_0$ and/or the gradient field, for example, or directly to a change in the system frequency.

An output frequency of an output signal from the high frequency generator can be controlled by a digital frequency variable. A counter- or division factor of a frequency synthesizer, for example, is a conceivable frequency variable. A synthesis signal with the system frequency is generated as a function of the output signal. It is possible here, for example, for the synthesis signal to be generated by mixing with or multiplying by the output signal, but it is equally possible for the output signal itself to be the synthesis signal or for the synthesis signal to be derived therefrom by linear or non-linear processing.

The frequency control device is designed to detect a temperature change in the temperature using the temperature sensor. The frequency control device could be in a signal link with the temperature sensor and could digitalize an analog signal voltage. However, it would also be possible to have a digital bus system, through which the frequency control device receives digital measured values from the temperature sensor or sensors.

The frequency control device is further designed to interpolate a temperature-time function of the temperature using the temperature change that has been detected. In the simplest case, the frequency control device can carry out either a linear interpolation of the temperature changes that have been detected or a polynomial interpolation. Here the temperature-time function can provide relative temperature values for a predetermined output temperature or absolute temperature values.

A function that, for example, expresses other values as a function of time, which however, are derived from the temperature by only one factor or a simple function can also be seen as a temperature-time function. This could also be, for example, a frequency-time function where the dependence of the frequency on the temperature is predetermined by a constant or by a simple approximation function and in this way can be derived directly from the temperature-time function.

The frequency control device is also designed to determine a time at which a change in the digital frequency variables in the least significant bit brings about a change in the frequency of the synthesis signal that corresponds to a change in the system frequency caused by a temperature according to the interpolated temperature-time function. It is conceivable, for example, that the frequency control device includes a computation unit that solves the interpolated temperature-time function for a temperature value that corresponds to a change in the system frequency that occurs with a change in the least significant bit. An approximation function or a directly predetermined functional connection can equally well be preset for the dependence of the system frequency and frequency variable. The solution can ensue in an analytical manner or using an approximation method.

Here, the least significant bit is the least significant bit that is used in the frequency variable for targeted control of the frequency. It is conceivable that the frequency variable includes further bits that cause even smaller frequency changes but that are no longer taken into account due to a resolution that is no longer physically practical when setting the system frequency, for example, because the resolution is higher than the frequency noise from a master clock or a frequency inaccuracy of a synthesizer caused by phase noise. These bits can be set at zero for example or be provided with a dither pattern without going beyond the scope of the invention.

Finally the frequency control device is designed to change the digital frequency variable in the least significant bit at the specified time. In one embodiment, the specified time is also a specified time interval of a sequence of time intervals that is predetermined by a system clock or a sample rate and within which the specified time falls. Preferably, within a time interval with a change in the least significant bit, there will be one or a plurality of time intervals without a change in the least significant bit or more significant bits.

Advantageously, the magnetic resonance tomography system according to one embodiment is in a position to detect slight temperature changes in a reliable manner and yet, by synchronization with and adjustment of the frequency change in line with the internal system processes, to avoid any more substantial frequency shifts that could lead to image artifacts.

Further advantageous embodiments are set out in the dependent claims.

In a possible embodiment of the magnetic resonance tomography system, the magnetic resonance tomography system includes a plurality of temperature sensors and an averaging unit. The averaging unit is designed to determine the temperature change as a function of a mean value from the plurality of temperature sensors. For example, a plurality of temperature sensors can be arranged in different positions on the magnetic resonance tomography system. The averaging unit can form, for example, a simple arithmetic mean value for the measured values from the temperature sensors or can also carry out a weighting with factors that reflect an influence of the individual measured values on the system frequency.

Advantageously, the magnetic resonance tomography system according one embodiment makes it possible to acquire different temperature values and thus also take into account different influences of various components in the temperature compensation.

In a conceivable embodiment of the magnetic resonance tomography system, the averaging unit is designed to average the temperature change over a predetermined period. It is conceivable, for example, for measured values to be averaged over 1, 2, 5 or more seconds.

Due to the narrow bandwidth, even small frequency changes in a magnetic resonance tomography system in the range of a few milli-hertz to hertz are relevant. Accordingly, even temperature changes of fractions of a Kelvin can cause or require such frequency changes. In order to detect these small changes in a reliable manner and avoid generating any high noise components through the temperature compensation, the magnetic resonance tomography system according to one embodiment averages the temperature values over fairly long periods. At the same time, however, the interpolation according to one embodiment makes it possible to carry out frequency corrections even within the averaging intervals and therefore avoid any more substantial frequency shifts.

In a possible embodiment of the magnetic resonance tomography system, the system frequency is a frequency of an excitation signal $B_1$ for exciting nuclear spins in the magnetic resonance tomography system.

Advantageously, the magnetic resonance tomography system according to one embodiment constantly adapts the excitation pulses to a changing Larmor frequency, which changes, for example, as a result of temperature changes in the magnet housing and a resulting altered $B_0$-field, and thus ensures a constant image quality.

In a conceivable embodiment of the magnetic resonance tomography system, the temperature sensor determines a temperature that is dependent on a local temperature in a patient tube and/or on a gradient coil.

Advantageously, the temperature sensor detects a temperature that is dependent on a temperature in the patient tube and/or the gradient coil. This can be, for example, a temperature of the air in the patient tube or in direct vicinity of the gradient coil, a cooling fluid used in the gradient coils, and/or a temperature in direct contact with a wall of the patient tube or of the gradient coil. It is therefore not absolutely necessary to place the temperature sensors in specific places that are difficult to access or are unfavorable for other reasons.

In a possible embodiment of the magnetic resonance tomography system, the frequency control device is designed to detect output values for the magnetic resonance tomography system and take the output values into account in the interpolation of the temperature-time function. For example, provision can be made for the frequency control device to have a mean gradient current or a mean high frequency output.

The additional information enables the frequency control device to better interpolate the temperature-time function for future times and to carry out the frequency correction of the system frequency with greater precision. In particular, in this way, a delay due to heat transport and/or sudden changes in the heat input can be taken into account by using different sequences.

The method embodiments share the advantages of the embodiments of the magnetic resonance tomography system.

BRIEF DESCRIPTION OF THE DRAWINGS

Further advantages and details will emerge from the description that follows of exemplary embodiments in connection with the drawings. The drawings show:

FIG. 2 is a schematic flow chart for a method according to one embodiment.

DETAILED DESCRIPTION

Figure 1:
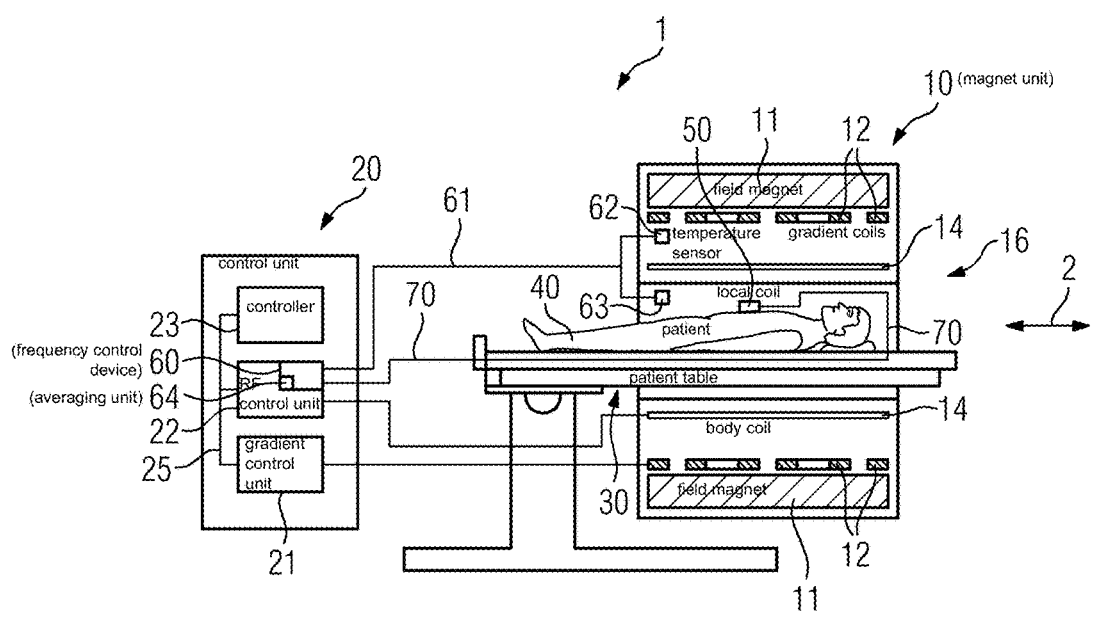
FIG. 1 is a schematic diagram of a magnetic resonance tomography system according to one embodiment.

FIG. 1 shows a schematic view of an embodiment of an resonance tomography system 1.

The magnet unit 10 includes a field magnet 11, which generates a static magnetic field $B_0$ for aligning nuclear spins of samples or in the body of a patient 40 in an accommodation region. The accommodation region is arranged in a patient tunnel 16 that extends through the magnet unit 10 in a longitudinal direction 2. The field magnet 11 is usually a superconducting magnet that can provide magnetic fields with a magnetic flow density of up to 3 T, and in the case of the latest equipment, even higher. For lower field strengths, however, permanent magnets or electromagnets with normally conductive coils can be used.

The magnet unit 10 further includes gradient coils 12 which, for spatial differentiation of the imaging regions acquired in the examination volume, are designed to superimpose variable magnetic fields in three spatial directions onto the magnetic field $B_0$. The gradient coils 12 are usually coils of normally conductive wires that can generate fields that are orthogonal to each other in the examination volume.

The magnet unit 10 also includes a body coil 14 that is designed to beam a high frequency signal supplied via a signal line into the examination volume and to receive resonance signals emitted by the patient 40 and transmit them via a signal line. Furthermore, the magnetic resonance tomography system according to some embodiments includes one or a plurality of local coils 50, which are arranged in the patient tunnel 16 close to the patient 40.

A control unit (controller) 20 supplies the magnet unit 10 with the various signals for the gradient coils 12 and the body coil 14 and evaluates the signals received.

The control unit 20 therefore includes a gradient control unit 21 that is designed to supply the gradient coils 12 via supply lines with variable currents that provide the desired gradient fields in the examination volume in a time-coordinated manner.

Furthermore, the control unit 20 includes a high frequency unit (controller) 22 designed to generate a high frequency pulse with a predetermined chronological sequence, amplitude and spectral output distribution to excite a magnetic resonance of the nuclear spins in the patient 40. Pulse outputs in the kilowatt range can be achieved in this case. For this purpose, the high frequency unit includes a high frequency generator, which can be implemented, for example, as a frequency synthesizer controlled by numerical values. The individual units are connected to one another via a signal bus 25.

The high frequency signal generated by the high frequency unit 22 is supplied via a signal link 70 in the patient couch 30 and disseminated to one or a plurality of local coils 50 and transmitted into the body of the patient 40 in order to generate the nuclear spins there. An emission of the high frequency signal via the body coil 14 is also conceivable, however.

The local coil 50 then preferably receives a magnetic resonance signal from the body of the patient 40 because, due to the close distance, the signal-to-noise ratio (SNR) in the local coil 50 is better than with reception through the body coil 14. The MR-signal received by the local coil 50 is prepared in the local coil 50 and forwarded to the high frequency unit 22 of the magnetic resonance tomography system 1 for evaluation and image acquisition. Preferably, the signal link 70 is likewise used for this purpose, but separate signal links or wireless transmission are also conceivable. It is equally conceivable for dedicated local coils or other antennas to be provided for receiving signals.

Through both the high frequency excitation pulses and the currents that flow through the gradient coils 12, electrical outputs on a kilowatt scale are introduced into the magnet unit 10, a considerable proportion of which are converted into heat, for example by the ohm losses in the gradient coils, by the eddy currents generated by the gradient fields in metallic housing components of the patient tunnel 14, or by radio waves absorbed by the patient 40. The heat generated leads to different temperature changes in the magnet unit 10.

The magnetic properties of the various materials change with the temperature. For example, ferromagnetic materials lose their ferromagnetic properties above the Curie temperature and the value for the magnetic permeability varies considerably. In this way, the magnetic fields of the static magnet $B_0$ and the gradient fields $B_{x,y,z}$ are changed in a temperature-dependent manner, so that the respective Larmor frequency likewise changes. In order to compensate for these frequency changes, a frequency control device 60 is provided in the magnetic resonance tomography system 1.

In FIG. 1, the frequency control device (controller) 60 is shown as part of the high frequency unit 22, but the frequency control device 60 could also be provided, for example, as part of the control unit 22. The frequency control device 60 is first connected via a signal bus 61 to temperature sensors 62, 63 in a signal link in order to detect temperature changes using the temperature sensors 62, 63, and second to the high frequency unit 22, in order to compensate for the effects of the temperature change in the high frequency unit 22 by a frequency change. Here, the temperature sensors 62, 63 can be directly in thermal contact with the components, such as the gradient coils 12 or the cryostat around the patient accommodation that influence the magnetic field and hence the system frequency. It is also conceivable, however, for the temperature sensors to be in indirect thermal contact with these components, for example, through a heat conductor, a cooling fluid, through convection or infrared radiation. Accordingly, the temperature sensors 62, 63 can be metallic sensors, for example, such as a PT100 resistor, semi-conductor elements such as PTCs, or even other detectors such as pyroelectric elements.

In the high frequency unit 22, a system frequency of a high frequency generator is controlled by a digital frequency variable, which corresponds to a digitally encoded numerical value. A digital frequency variable is distinguished by the fact that a minimum frequency change is caused by a change in the least significant bit of the frequency variables. A frequency change with a smaller amount is not possible. Examples of such frequency variables are, for example, division or counter factors in a frequency synthesizer.

In the simplest case, the frequency variable can directly indicate the Larmor frequency. Frequently, however, in the send-receive mode, a frequency can be raised or lowered by mixing. In this case, it is also conceivable for the system frequency to set or influence one of the two frequencies that are mixed. A frequency multiplication or frequency division of the output signal from the high frequency generator is also conceivable. The synthesis signal is derived accordingly with the system frequency directly or also indirectly from the output signal of the high frequency generator, with the synthesis signal preferably having the Larmor frequency as a frequency in the send-and/or-receive mode. In this way, a shift in the local or global Larmor frequency caused by the change in temperature can be compensated for in the patient tunnel by the frequency control device 60.

Due to the narrow band nuclear spin resonances, even frequency changes in the parts-per-million (ppm) range have an effect on the imaging, that is, smaller by a factor of a million in terms of the Larmor frequency. Accordingly, even temperature changes smaller than 100, 10 or 5 milli-Kelvin may be relevant. Such small temperature changes are difficult to measure. Preferably, noise in the measured values from the temperature sensors 62, 63 is reduced by an averaging of the measured signals over a fairly long period. The frequency control device can therefore include a corresponding averaging unit 64 for the measured values from the temperature sensors 62, 63. The averaging unit 64 averages over time. Weighted averaging across a plurality of sensors is also conceivable, however.

It is possible that the temperature change in the averaging period may assume a value that causes a frequency change in the Larmor frequency, which to compensate for this requires a change in the frequency variables by an amount that corresponds to a change in a plurality of bits and therefore causes a frequency shift. The frequency shift in turn may have negative effects on the imaging. The concept underlying the present embodiment for avoiding this effect is therefore on the one hand to indeed carry out an averaging over time but on the other hand however, to implement in each case a change in the frequency variables if a minimum change is present that corresponds to a change in the least significant bit in the frequency variables.

The magnetic resonance tomography system 1 according to one embodiment achieves this by carrying out the method, which is set out in FIG. 2 in a schematic flow chart.

In a step S10, the frequency control device 60 first determines a temperature change in the temperature sensor 62, 63. Here, the temperature change relates to a change in a temperature that exerts an influence on a system frequency and hence on the imaging. It can be, for example, a temperature change in the temperature of the gradient coils 12 or on the surface of the cryostat that surrounds the patient tunnel 16. Magnetic or geometric properties of these components that change with the temperature will then also influence the magnetic field $B_0$ and/or the gradient fields. If the frequencies of the excitation pulse and/or of the receivers are not adjusted accordingly, the image acquired will be of poorer quality. The determination of the temperature change can ensue for one individual sensor or also for a plurality of sensors via a mean value, which can also be weighted. In addition to or instead of this, an averaging over time of the measured values can ensue when determining the temperature change in order to reduce short-term interference and noise components.

In a step S20, the frequency control device 60 interpolates a temperature-time function of the temperature using the temperature change that has been determined. The interpolation can ensue using a linear interpolation, a polynomial interpolation, or a different modeling function, the parameters of which are adjusted using the temperature changes that have been determined. If there are more measured values detected for the temperature changes than parameters to be adjusted, an optimization process such as LMS (Least Mean Square) can be used.

Furthermore, it is conceivable that the frequency control device 60 will use further input parameters in addition to the temperature changes that have been detected when determining the temperature-time function. For example, the frequency control device 60 can receive from the control unit 20 further data relevant to a future temperature curve. These are, for example, up-to-date currents flowing through the gradient coils 12 or the high frequency output of the excitation pulses. Furthermore, the control unit 20 can predict these values for future reference too form the sequences used and transmit them to the frequency control device 60. In a possible embodiment, the frequency control device 60 uses this data to determine the temperature-time function more accurately for future reference. In particular, if a changeover takes place between sequences or, for instance, breaks are required for operational procedures, the accuracy of the temperature-time function can be improved considerably by determination merely from the temperature changes that have been detected.

In a step S30, the frequency control device 60 determines a time at which a change in the digital frequency variable in the least significant bit brings about a change in the frequency of the synthesis signal. The frequency control device 60 has been informed of the nature of the link between the frequency variable and the frequency. This can already be predetermined, for example, when developing the hardware and software for the magnetic resonance tomography system 1, using a constant of proportionality that is preset at the design stage. In this way, the frequency control device 60 can determine which frequency change in the system frequency corresponds to a change in the least significant bit in the frequency variable. The frequency control device 60 further has at its disposal a function or relationship between a temperature change and a change in the system frequency, which function can be provided to the frequency control device 60, for example, as a model function or as a table of values using model-based calculations or measurements. Using the temperature-time function, the frequency control device 60 is therefore able to determine the time at which the temperature change corresponds with a frequency change in the system frequency, which corresponds with a change in the least significant bit.

In a step S40, the frequency control device 60 finally changes the digital frequency variable in the least significant bit at the specified time. The specified time does not necessarily have to directly correspond with a time at which new measured values for the temperature change are determined. Rather, the adjustment of the frequency variables can ensue as a result thereof in small steps at many times between the determination of the measured values if the temperature change rate and the resulting frequency change rate in the system frequency is high and in this way a greater frequency shift at larger time intervals can be avoided. In the context of the present embodiments, the time can also be seen as a time interval that is predetermined by a system clock in the magnetic resonance tomography system 1 and in which the value determined from the temperature-time function occurs. Preferably, between the time intervals where a change in the frequency variables occurs, there will be one or a plurality of time intervals without a change in the frequency variables. The time intervals can, for example, be equivalent to milliseconds or multiples of a system clock and be consecutive without overlapping or be only slightly overlapping.

In a step S50, an output signal from the high frequency generator is generated. The output frequency is dependent on a value of a digital frequency variable, and a synthesis signal with the system frequency is dependent on the output signal.

Although the invention has been illustrated and described in greater detail with the preferred exemplary embodiment, the invention is not restricted to the examples disclosed, and other variants can be derived therefrom by a person skilled in the art, without going beyond the scope of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A magnetic resonance tomography system comprising:
   a temperature sensor;
   a high frequency generator, wherein a system frequency of the magnetic resonance tomography system has a temperature dependence on a temperature and the temperature sensor is configured to determine this temperature, wherein an output frequency of an output signal from the high frequency generator is controlled by a digital frequency variable and a synthesis signal is generated with the system frequency depending on the output signal; and
   a frequency controller configured to:
   determine the temperature change in the temperature using the temperature sensor;
   interpolate a temperature-time function of the temperature using the determined temperature change;
   determine a time at which a change in the digital frequency variables in a least significant bit brings about a change in the frequency of the synthesis signal that corresponds with a change in the system frequency through the temperature according to the interpolated temperature-time function; and
   change the digital frequency variable in the least significant bit at the specified time.

2. The magnetic resonance tomography system as claimed in claim 1, further comprising:
   one or more additional temperature sensors; and
   an averager, wherein the averager is configured to determine the temperature change as a function of a mean value for the temperature sensor and the additional temperature sensors.

3. The magnetic resonance tomography system as claimed in claim 2, wherein the averager is configured to average the temperature change over a predetermined time period.

4. The magnetic resonance tomography system as claimed in claim 3, wherein the system frequency indicates a frequency of an excitation signal $B_1$ for exciting nuclear spins in the magnetic resonance tomography system.

5. The magnetic resonance tomography system as claimed in claim 4, wherein the temperature sensor is configured to determine a temperature depending on a local temperature in a patient tunnel and/or on a gradient coil.

6. The magnetic resonance tomography system as claimed in claim 5, wherein the frequency controller is configured to detect output values for the magnetic resonance tomography system and take the output values into account when interpolating the temperature-time function.

7. The magnetic resonance tomography system as claimed in claim 1, wherein the system frequency is a frequency of an excitation signal $B_1$ for exciting nuclear spins in the magnetic resonance tomography system.

8. The magnetic resonance tomography system as claimed in claim 1, wherein the temperature sensor is configured to determine a temperature depending on a local temperature in a patient tunnel and/or on a gradient coil.

9. The magnetic resonance tomography system as claimed in claim 1, wherein the frequency controller is configured to detect output values for the magnetic resonance tomography system and take the output values into account when interpolating the temperature-time function.

10. A method for operating a magnetic resonance tomography system wherein the magnetic resonance tomography system comprises a frequency controller for temperature compensation, a temperature sensor, and a high frequency generator, wherein a system frequency of the magnetic resonance tomography system has a temperature dependence on a temperature, the method comprising:
   determining a temperature change in the temperature by the frequency controller using the temperature sensor;
   interpolating a temperature-time function for the temperature using the determined temperature change;
   determining a time at which a change in the digital frequency variables in a least significant bit brings about a change in the frequency of the synthesis signal that corresponds to a change in the system frequency due to the temperature according to the interpolated temperature-time function;
   changing the digital frequency variable in the least significant bit at the specified time; and
   generating an output signal from the high frequency generator, wherein an output frequency of the output signal is dependent on a digital frequency variable value, and wherein a synthesis signal with the system frequency is dependent on the output signal.

11. The method as claimed in claim 10, further comprising:
   determining the temperature change as a function of a mean value for the temperature sensor and an additional temperature sensor.

12. The method as claimed in claim 11, further comprising: averaging the temperature change over a predetermined time period.

13. The method as claimed in claim 10, wherein the system frequency is a frequency of an excitation signal $B_1$ for exciting nuclear spins in the magnetic resonance tomography system.

14. The method as claimed in claim 10, wherein determining the temperature change comprises determining a temperature depending on a local temperature in a patient tunnel and/or on a gradient coil.

15. The method as claimed in claim 10, wherein the frequency controller detects output values for the magnetic resonance tomography system and takes the output values into account when interpolating the temperature-time function.

16. A non-transitory computer-readable storage medium, on which is stored electronically readable control data executable by a controller of a magnetic resonance tomography system, the control data comprising instructions for:
   determining a temperature change in the temperature by a frequency controller using a temperature sensor;
   interpolating a temperature-time function for the temperature using the determined temperature change;
   determining a time at which a change in the digital frequency variables in a least significant bit brings about a change in the frequency of the synthesis signal that corresponds to a change in a system frequency due to the temperature according to the interpolated temperature-time function;
   changing the digital frequency variable in the least significant bit at the specified time; and
   generating an output signal from a high frequency generator, wherein an output frequency of the output signal is dependent on a digital frequency variable value, and wherein a synthesis signal with the system frequency is dependent on the output signal.

17. The non-transitory computer-readable storage medium of claim 16, wherein the instructions further comprise:
   determining the temperature change as a function of a mean value for the temperature sensor and an additional temperature sensor.

18. The non-transitory The computer-readable storage medium of claim 16, wherein the instructions further comprise:
   averaging the temperature change over a predetermined time period.

19. The non-transitory The computer-readable storage medium of claim 16, wherein the instructions further comprise:
   determining the temperature based on a local temperature in a patient tunnel and/or on a gradient coil.

20. The non-transitory The computer-readable storage medium of claim 16, wherein the instructions further comprise:
   detecting output values for the magnetic resonance tomography system and taking the output values into account when interpolating the temperature-time function.

* * * * *